US012661197B2

(12) United States Patent
Nowlin et al.

(10) Patent No.: US 12,661,197 B2
(45) Date of Patent: *Jun. 23, 2026

(54) TELEOPERATED SURGICAL SYSTEM WITH PATIENT HEALTH RECORDS BASED INSTRUMENT CONTROL

(71) Applicant: Intuitive Surgical Operations, Inc., Sunnyvale, CA (US)

(72) Inventors: William C. Nowlin, Los Altos Hills, CA (US); Mahdi Azizian, San Jose, CA (US); Simon P. DiMaio, San Carlos, CA (US); Brian D. Hoffman, Mountain View, CA (US); Paul W. Mohr, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/903,768

(22) Filed: Oct. 1, 2024

(65) Prior Publication Data

US 2025/0017673 A1      Jan. 16, 2025

Related U.S. Application Data

(63) Continuation of application No. 16/349,196, filed as application No. PCT/US2017/061131 on Nov. 10, 2017, now Pat. No. 12,133,702.

(Continued)

(51) Int. Cl.
A61B 34/35          (2016.01)
A61B 34/00          (2016.01)
(Continued)

(52) U.S. Cl.
CPC .............. *A61B 34/35* (2016.02); *A61B 34/10* (2016.02); *A61B 34/20* (2016.02); *A61B 34/25* (2016.02);
(Continued)

(58) Field of Classification Search
CPC ........... A61B 2017/00477; A61B 2018/00595; A61B 2018/00988; A61B 2034/107;
(Continued)

(56) References Cited

U.S. PATENT DOCUMENTS 8,147,503 B2    4/2012  Zhao et al.
8,419,717 B2    4/2013  Diolaiti et al.
(Continued)

FOREIGN PATENT DOCUMENTS

CN          103417299 A      12/2013
JP        2003067486 A       3/2003
(Continued)

OTHER PUBLICATIONS

Extended European Search Report for Application No. EP17870331. 0, mailed on May 29, 2020, 7 pages.
(Continued)

*Primary Examiner* — Christopher L Cook
(74) *Attorney, Agent, or Firm* — Foley & Lardner LLP

(57)          ABSTRACT

A method is provided for intra-surgical use of a surgical patient health record in a teleoperated surgical system that includes a surgical instrument and a surgical instrument actuator, comprising: receiving user input commands to control movement of a robotic surgical instrument; tracking robotic surgical instrument actuator state in response to the user input commands; and transitioning robotic surgical instrument actuator state to a safety mode in response to the robotic surgical instrument transitioning to a prescribed actuator state.

20 Claims, 11 Drawing Sheets

Related U.S. Application Data

(60) Provisional application No. 62/421,064, filed on Nov. 11, 2016.

(51) Int. Cl.

| | |
|---|---|
| *A61B 34/10* | (2016.01) |
| *A61B 34/20* | (2016.01) |
| *A61B 34/37* | (2016.01) |
| *A61B 90/00* | (2016.01) |
| *G16H 20/40* | (2018.01) |
| *G16H 40/67* | (2018.01) |
| *A61B 17/00* | (2006.01) |
| *A61B 18/00* | (2006.01) |

(52) U.S. Cl.
CPC .............. *A61B 34/37* (2016.02); *A61B 90/37* (2016.02); *G16H 20/40* (2018.01); *G16H 40/67* (2018.01); *A61B 2017/00477* (2013.01); *A61B 2018/00595* (2013.01); *A61B 2018/00988* (2013.01); *A61B 2034/107* (2016.02); *A61B 2034/252* (2016.02); *A61B 2034/254* (2016.02); *A61B 2034/256* (2016.02); *A61B 2090/031* (2016.02)

(58) Field of Classification Search
CPC ........ A61B 2034/252; A61B 2034/254; A61B 2034/256; A61B 2090/031; A61B 34/10; A61B 34/20; A61B 34/25; A61B 34/35; A61B 34/37; A61B 90/37; G16H 20/40; G16H 40/67

See application file for complete search history.

(56) References Cited

U.S. PATENT DOCUMENTS

| | | | |
|---|---|---|---|
| 8,681,095 | B2 | 3/2014 | Ogawa et al. |
| 9,649,164 | B2 | 5/2017 | Kim et al. |
| 2002/0038085 | A1 | 3/2002 | Immerz |
| 2002/0120188 | A1 | 8/2002 | Brock et al. |
| 2006/0142657 | A1 | 6/2006 | Quaid et al. |
| 2013/0041368 | A1 | 2/2013 | Cunningham et al. |
| 2013/0249695 | A1 | 9/2013 | Hann |
| 2014/0005684 | A1 | 1/2014 | Kim et al. |
| 2014/0374476 | A1 | 12/2014 | Ban et al. |
| 2016/0250751 | A1 | 9/2016 | Martinson et al. |
| 2016/0331474 | A1 | 11/2016 | Lacal et al. |
| 2017/0360509 | A1 | 12/2017 | Bonny et al. |
| 2018/0085175 | A1 | 3/2018 | Steinle et al. |
| 2018/0271603 | A1 | 9/2018 | Nir et al. |
| 2019/0282311 | A1 | 9/2019 | Nowlin et al. |

FOREIGN PATENT DOCUMENTS

| | | | |
|---|---|---|---|
| JP | 2005312991 | A | 11/2005 |
| JP | 2007075518 | A | 3/2007 |
| JP | 2007111126 | A | 5/2007 |
| JP | 2011206180 | A | 10/2011 |
| KR | 20120126679 | A | 11/2012 |
| WO | WO-2006020792 | A2 | 2/2006 |

OTHER PUBLICATIONS

International Preliminary Report on Patentability for Application No. PCT/US2017/061131, mailed on May 23, 2019, 7 pages.
International Search Report and Written Opinion for Application No. PCT/US2017/061131, mailed on Mar. 2, 2018, 16 pages.
Jakopec M., et al., "Acrobot: A "Hands-on" Robot Fortotal Knee Replacement Surgery," IEEE, 2002, pp. 116-120.
Office Action for Chinese Application No. 201780073360.6, mailed on Jan. 4, 2022 with English translation, 22 pages.
Office Action for Chinese Application No. CN20178073360, mailed Jun. 14, 2022, 13 pages.
Office Action for Japanese Application No. JP20190524330, mailed Apr. 19, 2022, 9 pages.
Office Action for Korean Application No. KR20197016197, mailed Apr. 21, 2022, 17 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

1004

1018

| Time Stamp | Video Segment | Actuator State |
|---|---|---|
| $t_1$ | Video Image 1 | Actuator State 1 |
| $t_2$ | Video Image 2 | Actuator State 2 |
| ⋮ | ⋮ | ⋮ |
| $t_n$ | Video Image n | Actuator State n |

1020　1004

| HR Characteristic | Surgical NSK Stage | Surgical Instrument Actuation State | Message | Surgical Instrument Safety Actuation State |
|---|---|---|---|---|
| 1 | Stage1/ Risk1 | X | A | L |
| 2 | --- | -- | --- | --- |
| 3 | Stage3/ Risk2 | Y | B | M |
| 4 | --- | -- | --- | --- |
| 5 | Stage5/ Risk3 | Z | C | N |

FIG. 13

TELEOPERATED SURGICAL SYSTEM WITH PATIENT HEALTH RECORDS BASED INSTRUMENT CONTROL

CLAIM OF PRIORITY

This application is a continuation of and claims the priority to U.S. patent application Ser. No. 16/349,196, filed on May 10, 2019, which claims the benefit and priority of International Application No, PCT/US2017/061131, filed on Nov. 10, 2017, which claims the benefit of priority to U.S. Patent Application No. 62/421,064, filed on Nov. 11, 2016, the contents of all of which are hereby incorporated herein by reference in their entireties for all purposes.

BACKGROUND

Field of Invention

Inventive aspects are associated with medical devices used during surgery. More specifically, aspects are associated with surgical planning tools implemented on a medical device in communication with a video library database.

Art

Surgeons typically undertake extensive study before performing a surgical procedure. Traditionally, surgeons were limited to the study of generic anatomical models, such as photographs or drawings. More recently, various pre-operative diagnostic procedures (e.g., x-ray, CT, MRI, etc.) have made patient-specific anatomical information available.

In some cases, it is desirable to make additional, relevant anatomic and surgical procedure information available to a surgeon. In one aspect, it is desirable to provide a surgeon planning an operation on a particular patient with a surgical site video recording of an earlier surgical procedure performed on the particular patient. In another aspect, it is desirable to provide a surgeon with one or more surgical video recordings of surgical procedures on other patients that are similar to the surgical procedure planned for a particular patient. In one aspect, it is desirable to provide such information to a surgeon prior to the surgeon undertaking a particular surgical procedure. And in another aspect, it may be desirable to provide this information to a surgeon intraoperatively.

In one aspect, it is desirable to configure a video database that includes intraoperative surgical site video recordings of various procedures undergone by various patients. In one aspect, it is desirable to configure a medical device capable of video recording to further include an input that enables a surgeon using the medical device to highlight and annotate the video recording in real time as it is being recorded. In one aspect, it is desirable to configure a computer-based pattern matching algorithm to search through the individual records of the video database, identify relevant video records, and provide a surgeon with this relevant information for a particular surgical procedure.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

A method is provided for intra-surgical use of a surgical patient health record in a teleoperated surgical system that includes a surgical instrument and a surgical instrument actuator. User input commands are received from a user to control movement of a robotic surgical instrument. Actuator state of surgical instrument actuator state of the robotic instrument is tracked during movement of the robotic surgical instrument in response to the user input commands. Surgical instrument actuator state of the robotic instrument is transitioned to a safety mode in response to the robotic surgical instrument transitioning to a prescribed actuator state.

BRIEF DESCRIPTION OF THE DRAWINGS

FIG. 13 is an illustrative drawing representing an example eighth information structure of the atlas stored in the computer readable storage device that corresponds to a particular surgical procedure and that associates different example surgical patient health record characteristics with surgical risk management information in accordance with some embodiments.

DETAILED DESCRIPTION

Figure 1:
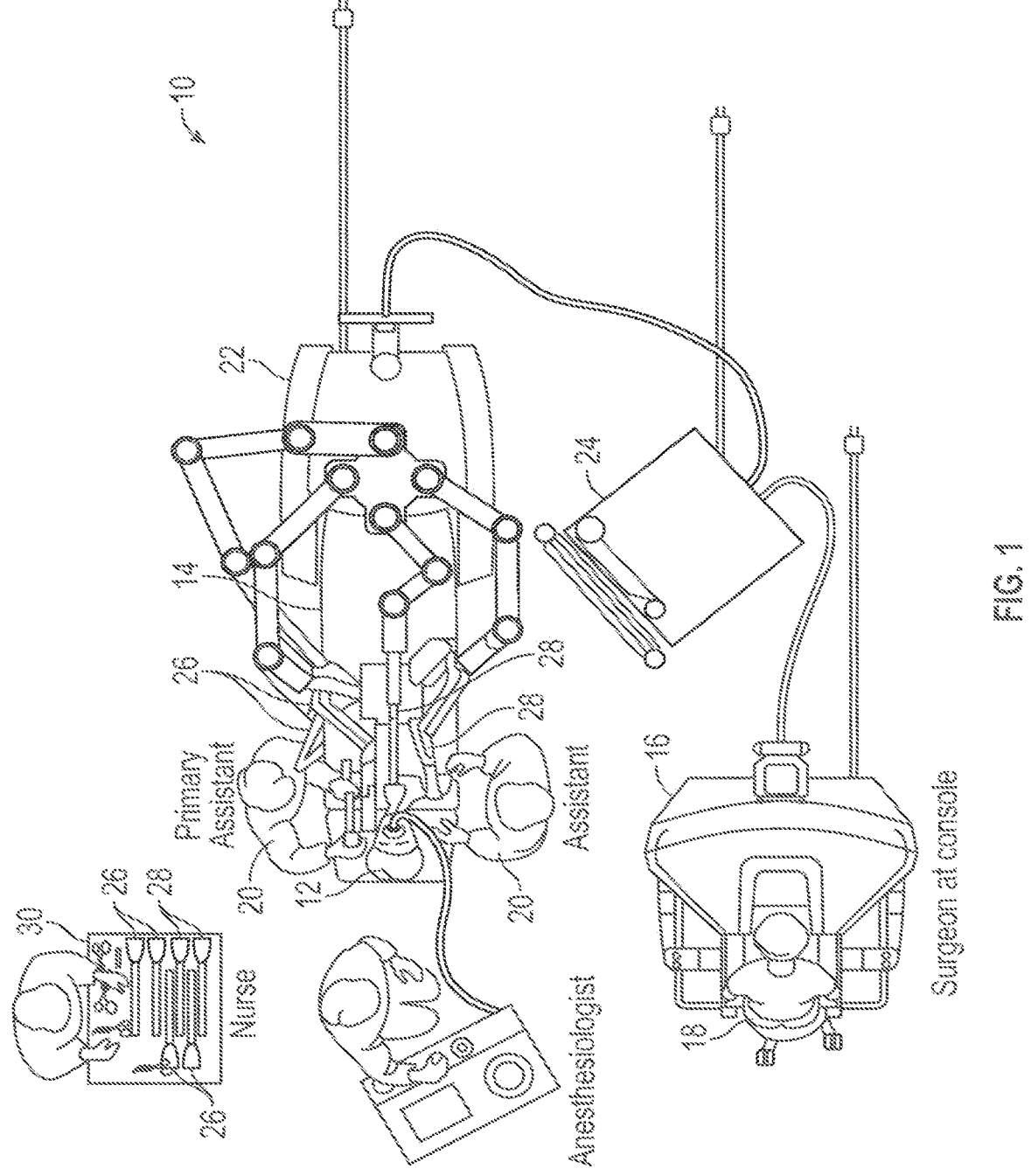
FIG. 1 is a plan view of a minimally invasive teleoperated surgical system.

This description and the accompanying drawings that illustrate inventive aspects, embodiments, implementations, or applications should not be taken as limiting—the claims define the protected invention. Various mechanical, compositional, structural, electrical, and operational changes may be made without departing from scope of this description and the claims. In some instances, well-known circuits, structures, or techniques have not been shown or described in detail in order not to obscure the invention. Like numbers in two or more figures represent the same or similar elements.

Elements described in detail with reference to one embodiment, implementation, or application may, whenever practical, be included in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Aspects of the invention are described primarily in terms of an implementation using a da Vinci® Surgical System (specifically, a Model IS4000, marketed as the da Vinci® Xi™ HID™ Surgical System), commercialized by Intuitive Surgical, Inc. of Sunnyvale, California. Knowledgeable persons will understand, however, that inventive aspects disclosed herein may be embodied and implemented in various ways, including robotic and, if applicable, non-robotic embodiments and implementations. Implementations on da Vinci® Surgical Systems (e.g., the Model IS4000 da Vinci® Xi™ Surgical System, the Model IS3000 da Vinci Si® Surgical System) are merely exemplary and are not to be considered as limiting the scope of the inventive aspects disclosed herein.

In accordance with various aspects, the present disclosure describes a surgical planning tool that includes a medical device configured to video record the performance of surgical procedures. The video recordings can be embedded with various metadata, e.g., highlights made by a medical person. Additionally, the video recordings can be tagged with various metadata, e.g., text annotations describing certain subject matter of the video, the identity of the patient to whom the video recording corresponds, biographical or medical information about the patient, and the like. In one aspect, tagged metadata is embedded in the video recordings.

In accordance with further aspects, the present disclosure describes a teleoperated medical device that includes a surgical instrument used in one or more stages of a surgical procedure. Different stages of a surgical procedure may be associated with different risk levels to different patients. In some embodiments, a risk level to a patient may be determined based at least in part upon patient's health record, either manually by a medical person, or automatically via an expert system or artificial intelligence. The surgical instrument is controlled by one or more surgical instrument actuators operable in multiple actuator states. An actuator state of an actuator controlling a surgical instrument is tracked during surgical procedures. In some embodiments, an information structure in a computer readable storage device associates surgical instrument actuator states with surgical guidance information for presentation to a surgeon in response to a surgical instrument transitioning to a state in which a patient is at a potentially increased risk during a surgical procedure. In some embodiments, the surgical guidance information that is presented to a surgeon is determined based at least in part upon a surgical patient's health record. In some embodiments, an information structure in a computer readable storage device associates surgical instrument actuator states with safety transition information for use to cause a surgical instrument actuator to transition to an actuator safety mode of operation in which a patient is at less risk, and therefore safer, at least with respect to some aspect of a surgical procedure. In some embodiments, the surgical instrument actuator safety mode of operation is determined based at least in part upon a surgical patient's health record.

The video recordings and information structures that associate surgical instrument actuator states with surgical guidance or actuator safety mode information can be archived on an electronic medical record database implemented locally or on a cloud data storage service. The video recordings can be made available to interested health care providers. The information structures can be made available for use with the teleoperated medical device to provide surgical guidance and to control surgical instrument actuator state during performance of surgical procedures.

Health care providers can search the medical device database based upon patient heath care records for videos and information structure relationships of interest using the metadata tags described above. Additionally, in one aspect, the surgical planning tool includes a computer-based pattern matching and analysis algorithm. In one aspect, the pattern-matching algorithm culls through the videos stored on the electronic medical record database to identify correlations between visual characteristics in the video recordings and associated metadata tags made by medical persons. The surgical planning tool can apply these correlations to newly encountered anatomy, and thereby assist medical persons performing a procedure in making determinations about patient anatomy, preferred surgical approaches, disease states, potential complications, etc. In another aspect, the pattern matching algorithm culls through videos stored on the electronic medical record database (either private or public or both) to identify correlations between visual characteristics in the video recordings and patient health record information to identify anatomical characteristics that correlate with health record information. The surgical planning tool can apply these correlations between anatomy and health care records to a current patient's anatomy and health records, and thereby assist medical persons planning and performing a surgical procedure involving the current patient.

Minimally Invasive Teleoperated Surgical System

Referring now to the drawings, in which like reference numerals represent like parts throughout the several views, FIG. 1 is a plan view of a minimally invasive teleoperated surgical system 10, typically used for performing a minimally invasive diagnostic or surgical procedure on a patient 12 who is lying on an operating table 14. The system includes a surgeon's console 16 for use by a surgeon 18 during the procedure. One or more assistants 20 may also participate in the procedure. The minimally invasive teleoperated surgical system 10 further includes a patient-side cart 22 and an electronics cart 24. The patient-side cart 22 can manipulate at least one removably coupled surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which can be manipulated by the patient-side cart 22 to orient the endoscope 28. Computer processors located on the electronics cart 24 can be used to process the images of the surgical site for subsequent display to the surgeon 18 through the surgeon's console 16. The number of surgical instruments 26 used at one time will generally depend on the diagnostic or surgical procedure and the space constraints within the operating room among other factors. If it is necessary to change one or more of the surgical instruments 26 being used during a procedure, an assistant 20 can remove the surgical instrument 26 from the patient-side cart 22, and replace it with another surgical instrument 26 from a tray 30 in the operating room.

Figure 2:
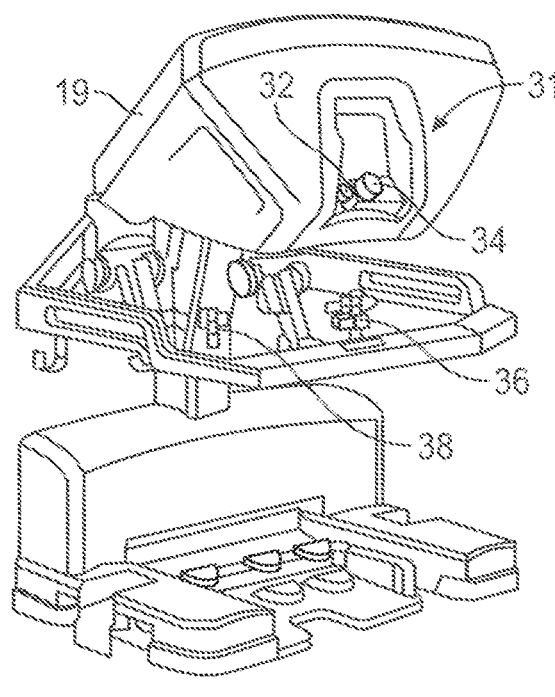
FIG. 2 is a perspective view of a surgeon's console.

FIG. 2 is a perspective view of the surgeon's console 16. The surgeon's console 16 includes a left eye display 32 and a right eye display 34 for presenting the surgeon 18 with a coordinated stereoscopic view of the surgical site that enables depth perception. The console 16 further includes one or more control inputs 36. One or more surgical instruments installed for use on the patient-side cart 22 (shown in FIG. 1) move in response to surgeon 18's manipulation of the one or more control inputs 36. The control inputs 36 can provide the same mechanical degrees of freedom as their associated surgical instruments 26 (shown in FIG. 1) to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36.

The surgeon's console 16 is usually located in the same room as the patient so that the surgeon can directly monitor the procedure, be physically present if necessary, and speak to a patient-side assistant directly rather than over the telephone or other communication medium. But, the surgeon can be located in a different room, a completely different building, or other remote location from the patient allowing for remote surgical procedures.

Figure 3:
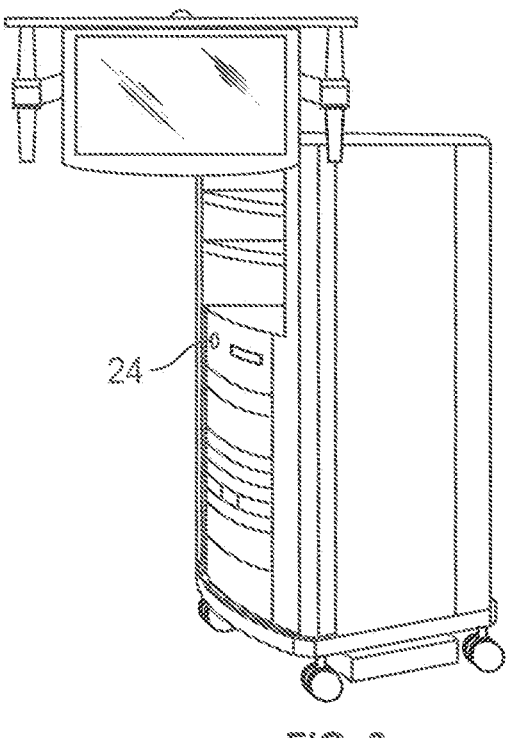
FIG. 3 is a perspective view of an electronics cart.

FIG. 3 is a perspective view of the electronics cart 24. The electronics cart 24 can be coupled with the endoscope 28 and includes a computer processor to process captured images for subsequent display, such as to a surgeon on the surgeon's console, or on another suitable display located locally and/or remotely. For example, if a stereoscopic endoscope is used, a computer processor on electronics cart 24 can process the captured images to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations. Optionally, equipment in electronics cart may be integrated into the surgeon's console or the patient-side cart, or it may be distributed in various other locations in the operating room.

Figure 4:
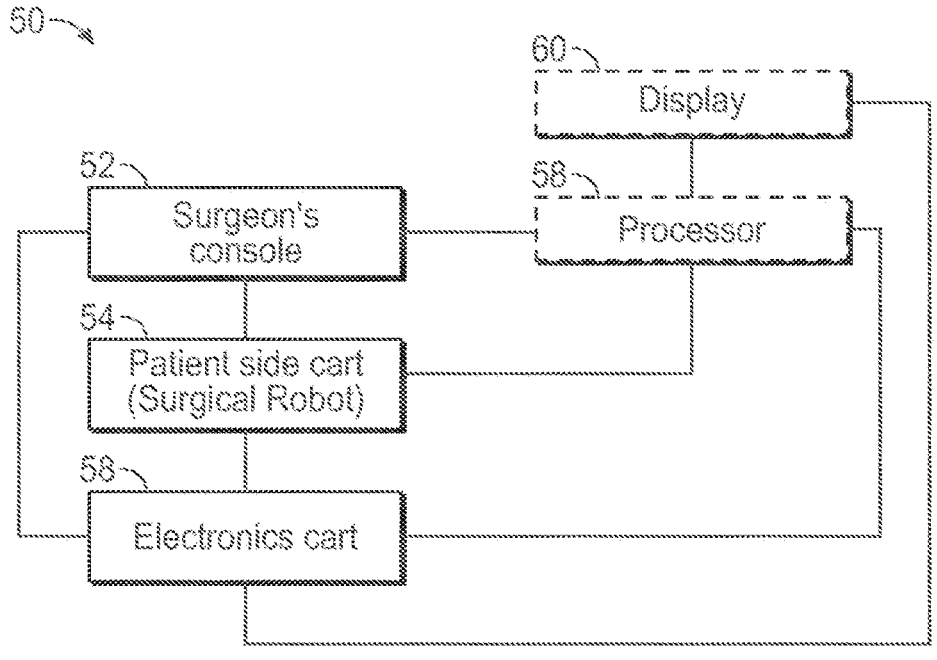
FIG. 4 is a diagrammatic illustration of a teleoperated surgical system.

FIG. 4 diagrammatically illustrates a teleoperated surgical system 50 (such as the minimally invasive teleoperated surgical system 10 of FIG. 1). A surgeon's console 52 (such as surgeon's console 16 in FIG. 1) can be used by a surgeon to control a patient-side cart 54 (such as patient-side cart 22 in FIG. 1) during a minimally invasive procedure. The patient-side cart 54 can use an imaging device, such as a stereoscopic endoscope, to capture images of a surgical site and output the captured images to a computer processor located on an electronics cart 56 (such as the electronics cart 24 in FIG. 1). The computer processor typically includes one or more data processing boards purposed for executing computer readable code stored in a non-volatile memory device of the computer processor. In one aspect, the computer processor can process the captured images in a variety of ways prior to any subsequent display. For example, the computer processor can overlay the captured images with a virtual control interface prior to displaying the combined images to the surgeon via the surgeon's console 52.

Additionally, or in the alternative, the captured images can undergo image processing by a computer processor located outside of electronics cart 56. In one aspect, teleoperated surgical system 50 includes an optional computer processor 58 (as indicated by dashed line) similar to the computer processor located on electronics cart 56, and patient-side cart 54 outputs the captured images to computer processor 58 for image processing prior to display on the surgeon's console 52. In another aspect, captured images first undergo image processing by the computer processor on electronics cart 56 and then undergo additional image processing by computer processor 58 prior to display on the surgeon's console 52. Teleoperated surgical system 50 can include an optional display 60, as indicated by dashed line. Display 60 is coupled with the computer processor located on the electronics cart 56 and with computer processor 58, and captured images processed by these computer processors can be displayed on display 60 in addition to being displayed on a display of the surgeon's console 52.

Figure 5:
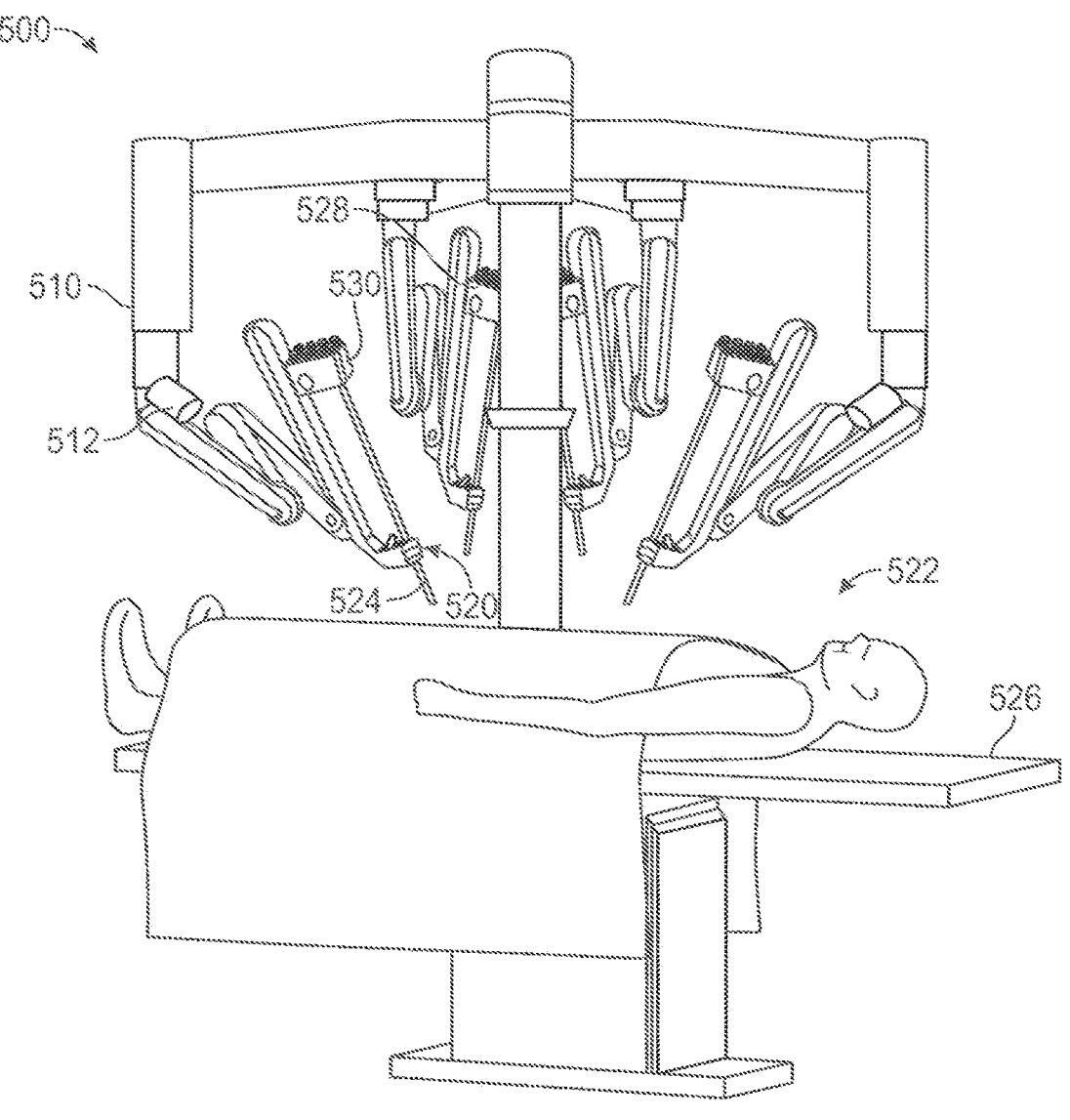
FIG. 5 is a perspective view of a patient-side cart.

FIG. 5 is a perspective view of a patient-side cart 500 of a minimally invasive teleoperated surgical system, in accordance with embodiments of the present invention. The patient-side cart 500 includes one or more support assemblies 510. A surgical instrument manipulator 512 is mounted at the end of each support assembly 510. Additionally, each support assembly 510 can optionally include one or more unpowered, lockable setup joints that are used to position the attached surgical instrument manipulator 512 with reference to the patient for surgery. As depicted, the patient-side cart 500 rests on the floor. In other embodiments, operative portions of the patient-side cart can be mounted to a wall, to the ceiling, to the operating table 526 that also supports the patient's body 522, or to other operating room equipment. Further, while the patient-side cart 500 is shown as including four surgical instrument manipulators 512, more or fewer surgical instrument manipulators 512 may be used.

A functional minimally invasive teleoperated surgical system will generally include a vision system portion that enables a user of the teleoperated surgical system to view the surgical site from outside the patient's body 522. The vision system typically includes a camera instrument 528 for capturing video images and one or more video displays for displaying the captured video images. In some surgical system configurations, the camera instrument 528 includes optics that transfer the images from a distal end of the camera instrument 528 to one or more imaging sensors (e.g., CCD or CMOS sensors) outside of the patient's body 522. Alternatively, the imaging sensor(s) can be positioned at the distal end of the camera instrument 528, and the signals produced by the sensor(s) can be transmitted along a lead or wirelessly for processing and display on the one or more video displays. One example of a video display is the stereoscopic display on the surgeon's console in surgical systems commercialized by Intuitive Surgical, Inc., Sunnyvale, California.

Referring to FIG. 5, mounted to each surgical instrument manipulator 512 is a surgical instrument 520 that operates at a surgical site within the patient's body 522. Each surgical instrument manipulator 512 can be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 512 to move its associated surgical instrument around a center of motion on the instrument that stays stationary with reference to the patient, and this center of motion is typically located at the position where the instrument enters the body.

In one aspect, surgical instruments 520 are controlled through computer-assisted teleoperation. A functional minimally invasive teleoperated surgical system includes a control input that receives inputs from a user of the teleoperated surgical system (e.g., a surgeon or other medical person). The control input is in communication with one or more computer-controlled teleoperated actuators, such as one or more motors to which surgical instrument 520 is coupled. In this manner, the surgical instrument 520 moves in response to a medical person's movements of the control input. In one aspect, one or more control inputs are included in a surgeon's console such as surgeon's console 16 shown at FIG. 2. A surgeon can manipulate control inputs 36 of surgeon's console 16 to operate teleoperated actuators of patient-side cart 500. The forces generated by the teleoperated actuators are transferred via drivetrain mechanisms, which transmit the forces from the teleoperated actuators to the surgical instrument 520.

Referring to FIG. 5, in one aspect, a surgical instrument 520 and a cannula 524 are removably coupled to manipulator 512, with the surgical instrument 520 inserted through the cannula 524. One or more teleoperated actuators of the manipulator 512 move the surgical instrument 512 as a whole. The manipulator 512 further includes an instrument carriage 530. The surgical instrument 520 is detachably connected to the instrument carriage 530. In one aspect, the instrument carriage 530 houses one or more teleoperated actuators inside that provide a number of controller motions that the surgical instrument 520 translates into a variety of movements of an end effector on the surgical instrument 520. Thus the teleoperated actuators in the instrument carriage 530 move only one or more components of the surgical instrument 520 rather than the instrument as a whole. Inputs to control either the instrument as a whole or the instrument's components are such that the input provided by a surgeon or other medical person to the control input (a "master" command) is translated into a corresponding action by the surgical instrument (a "slave" response).

In an alternate embodiment, instrument carriage 530 does not house teleoperated actuators. Teleoperated actuators that enable the variety of movements of the end effector of the surgical instrument 520 are housed in a location remote from the instrument carriage 530, e.g., elsewhere on patient-side cart 500. A cable-based force transmission mechanism or the like is used to transfer the motions of each of the remotely located teleoperated actuators to a corresponding instrument-interfacing actuator output located on instrument carriage 530. In some embodiments, the surgical instrument 520 is mechanically coupled to a first actuator, which controls a first motion of the surgical instrument such as longitudinal (z-axis) rotation. The surgical instrument 520 is mechanically coupled to a second actuator, which controls second motion of the surgical instrument such as two-dimensional (x, y) motion. The surgical instrument 520 is mechanically coupled to a third actuator, which controls third motion of the surgical instrument such as opening and closing or a jaws end effector.

Figure 6:
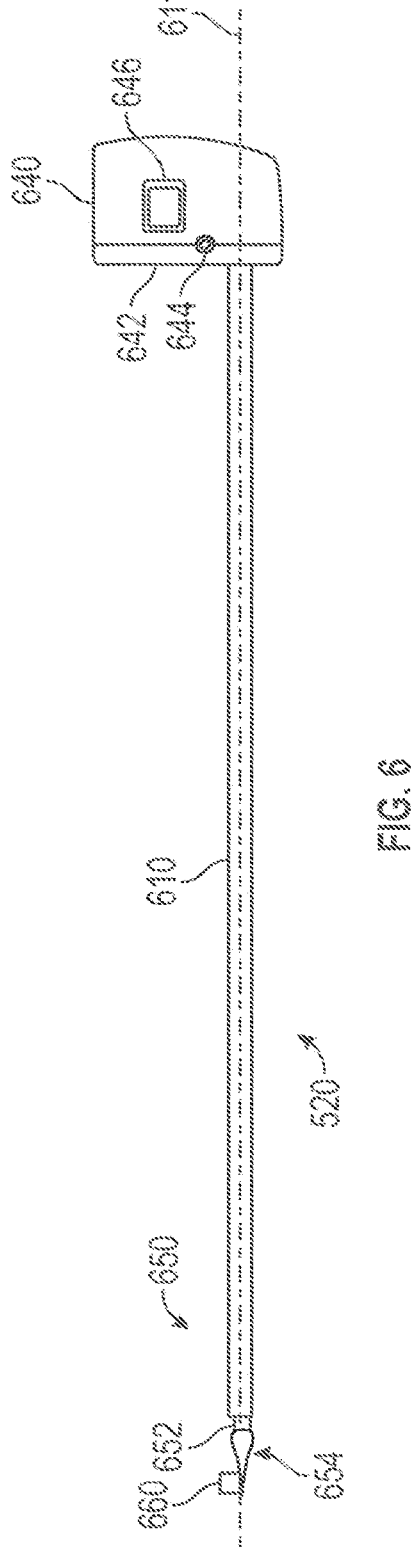
FIG. 6 is an elevation view of a surgical instrument.

FIG. 6 is a side view of a surgical instrument 520, which includes a distal portion 650 and a proximal control mechanism 640 coupled by an elongate tube 610 having an elongate tube centerline axis 611. The surgical instrument 520 is configured to be inserted into a patient's body and is used to carry out surgical or diagnostic procedures. The distal portion 650 of the surgical instrument 520 can provide any of a variety of end effectors 654, such as the forceps shown, a needle driver, a cautery device, a cutting tool, an imaging device (e.g., an endoscope or ultrasound probe), or the like. The surgical end effector 654 can include a functional mechanical degree of freedom, such as jaws that open or close, or a knife that translates along a path. In the embodiment shown, the end effector 654 is coupled to the elongate tube 610 by a wrist 652 that allows the end effector to be oriented relative to the elongate tube centerline axis 611. Surgical instrument 520 can also contain stored (e.g., on a semiconductor memory inside the instrument) information, which may be permanent or may be updatable by a surgical system configured to operate the surgical instrument 520. Accordingly, the surgical system may provide for either one-way or two-way information communication between the surgical instrument 520 and one or more components of the surgical system.

Figure 7:
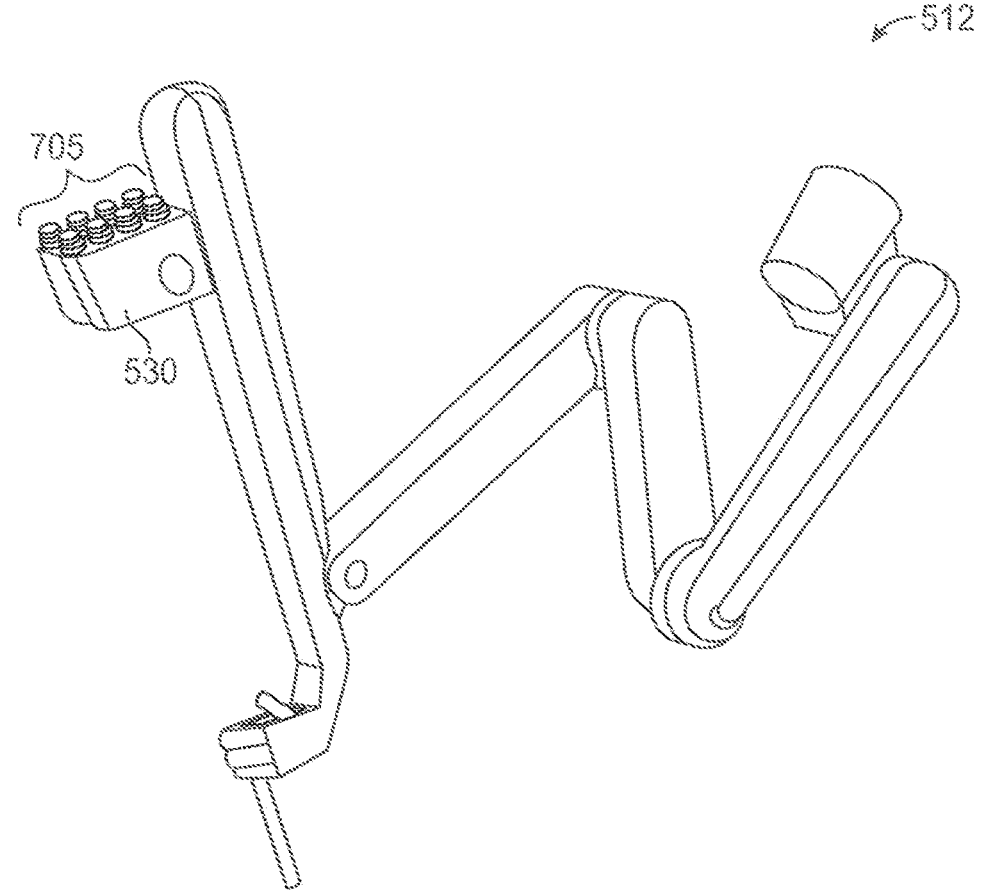
FIG. 7 is a perspective view of an instrument manipulator.

FIG. 7 is a perspective view of surgical instrument manipulator 512. Instrument manipulator 512 is shown with no surgical instrument installed. Instrument manipulator 512 includes an instrument carriage 530 to which a surgical instrument (e.g., surgical instrument 520) can be detachably connected. Instrument carriage 530 houses a plurality of teleoperated actuators. Each teleoperated actuator includes an actuator output 705. When a surgical instrument is installed onto instrument manipulator 512, one or more instrument inputs (not shown) of an instrument proximal control mechanism (e.g., proximal control mechanism 640 at FIG. 6) are mechanically coupled with corresponding actuator outputs 705. In one aspect, this mechanical coupling is direct, with actuator outputs 705 directly contacting corresponding instrument inputs. In another aspect, this mechanical coupling occurs through an intermediate interface, such as a component of a drape configured to provide a sterile barrier between the instrument manipulator 512 an associated surgical instrument.

In one aspect, movement of one or more instrument inputs by corresponding teleoperated actuators results in a movement of a surgical instrument mechanical degree of freedom. For example, in one aspect, the surgical instrument installed on instrument manipulator 512 is surgical instrument 520, shown at FIG. 6. Referring to FIG. 6, in one aspect, movement of one or more instrument inputs of proximal control mechanism 640 by corresponding teleoperated actuators rotates elongate tube 610 (and the attached wrist 652 and end effector 654) relative to the proximal control mechanism 640 about elongate tube centerline axis 611. In another aspect, movement of one or more instrument inputs by corresponding teleoperated actuators results in a movement of wrist 652, orienting the end effector 654 relative to the elongate tube centerline axis 611. In another aspect, movement of one or more instrument inputs by corresponding teleoperated actuators results in a movement of one or more moveable elements of the end effector 654 (e.g., a jaw member, a knife member, etc.). Accordingly, various mechanical degrees of freedom of a surgical instrument installed onto an instrument manipulator 512 can be moved by operation of the teleoperated actuators of instrument carriage 530.

Annotating a Recorded Video

Figure 8:
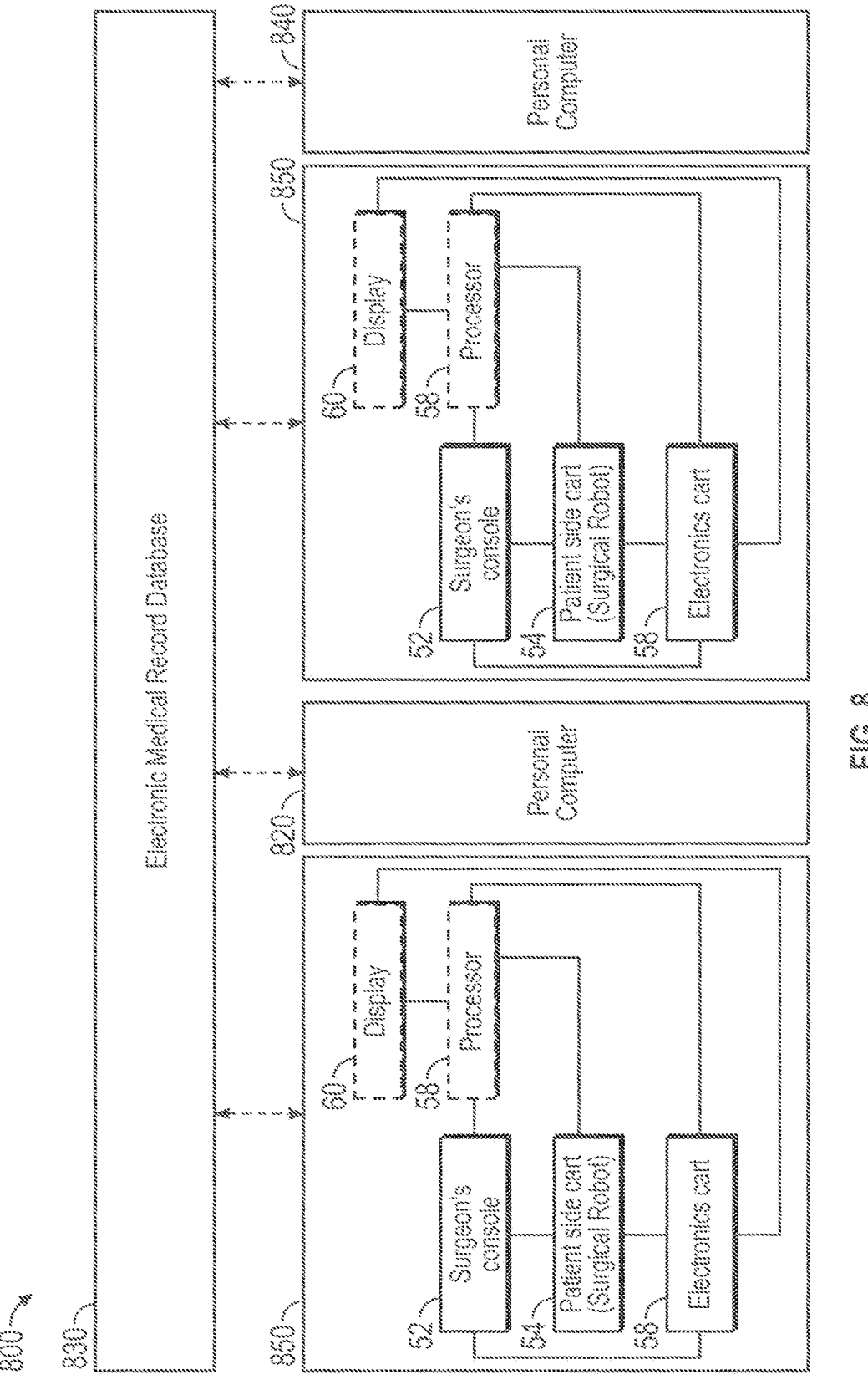
FIG. 8 is a diagrammatic illustration of a surgical planning tool.

FIG. 8 shows a schematic diagram of an exemplary surgical planning tool 800. In one aspect, surgical planning tool 800 includes a teleoperated surgical system 850 in data communication with an electronic medical device record database 830. Teleoperated surgical system 850 shown here is similar to teleoperated surgical system 850 shown at FIG. 4. In one aspect, electronic medical record database 830 includes the medical records of patients that have undergone treatment at a particular hospital. Database 830 can be implemented on a server located on-site at the hospital. The medical record entries contained in the database 830 can be accessed from hospital computers through an intranet network. Alternatively, database 830 can be implemented on a remote server located off-site from the hospital, e.g., using one of a number of cloud data storage services. In this case, medical record entries of database 830 are stored on the cloud server, and can be accessed by a computer with internet access.

In one aspect, a surgical procedure is performed on a first patient using teleoperated surgical system 850. An imaging device associated with teleoperated surgical system 850 captures images of the surgical site and displays the captured images as frames of a video on a display of surgeon's console 52. In one aspect, a medical person at surgeon's console 52 highlights or annotates certain patient anatomy shown in the displayed video using an input device of surgeon's console 52. An example of such an input device is control input 36 shown at FIG. 2, which is coupled to a cursor that operates in conjunction with a graphic user interface overlaid onto the displayed video. The graphic user interface can include a QWERTY keyboard, a pointing device such as a mouse and an interactive screen display, a touch-screen display, or other means for data or text entry, including repurposing any of the existing manipulators as an input device. Accordingly, the medical person can highlight certain tissue of interest in the displayed image or enter a text annotation.

In one aspect, the surgical site video is additionally displayed on a display located on electronics cart 56. In one aspect, the display of electronics cart is a touch-screen user interface usable by a medical person to highlight and annotate certain portions of patient anatomy shown on an image that is displayed for viewing on the display on the electronics cart. A user, by touching portions of patient anatomy displayed on the touch-screen user interface, can highlight portions of the displayed image. Additionally, a graphic interface including a QWERTY keyboard can be overlaid on the displayed image. A user can use the QWERTY keyboard to enter text annotations.

In one aspect, the surgical site video captured by the imaging device associated with teleoperated surgical system 850 is recorded by the teleoperated surgical system 850, and stored on database 830, in addition to being displayed in real time or near real time to a user. Highlights and/or annotations associated with the recorded video that were made by the user can also be stored on database 830. In one aspect, the highlights made by the user are embedded with the recorded video prior to its storage on database 830. At a later time, the recorded video can be retrieved for viewing. In one aspect, a viewer of the recorded video can select whether the highlights are displayed or suppressed from view. Similarly, annotations associated with the recorded video can also be stored on database 830. In one aspect, the annotations made by the user are used to tag the recorded video, and can be used to provide as a means of identifying the subject matter contained in the recorded video. For example, one annotation may describe conditions of a certain disease state. This annotation is used to tag the recorded video. At a later time, a person desiring to view recorded procedures concerning this disease state can locate the video using a key word search.

Retrieval of Stored Video

In some cases, it is desirable for a medical person to be able to view video recordings of past surgical procedures performed on a given patient. In one aspect, a patient who previously underwent a first surgical procedure to treat a medical condition subsequently requires a second surgical procedure to treat recurrence of the same medical condition or to treat anatomy located nearby to the surgical site of the first surgical procedure. In one aspect, the surgical site events of the first surgical procedure were captured in a surgical site video recording, and the video recording was archived in database 830 as part of the patient's electronic medical records. Prior to performing the second surgical procedure on the patient, a medical person can perform a search of database 830 to locate the video recording of the patient's earlier surgical procedure.

In some cases, it is desirable for a medical person planning to perform a surgical procedure on a patient to be able to view video recordings of similar surgical procedures performed on persons having certain characteristics similar to the patient. In one aspect, surgical site video recordings of surgical procedures can be tagged with metadata information such as the patient's age, gender, body mass index, genetic information, type of procedure the patient underwent, etc., before each video recording is archived in database 830. In one aspect, the metadata information used to tag a video recording is automatically retrieved from a patient's then-existing medical records, and then used to tag the video recording before the video recording is archived in database 830. Accordingly, prior to performing a medical procedure on a patient, a medical person can search database 830 for video recordings of similar procedures performed on patients sharing certain characteristics in common with the patient. For example, if the medical person is planning to use teleoperated surgical system 850 to perform a prostatectomy on a 65-year-old male patient with an elevated body mass index using, the medical person can search database 830 for surgical site video recordings of prostatectomies performed using teleoperated surgical system 850 on other males of similar age and having similarly elevated body mass index.

In one aspect, a video recording of a surgical procedure is communicated by database 830 to an optional personal computer 820 (as indicated by dashed line), and made available for viewing by a medical person who plans to perform a surgical procedure. Additionally, or in the alternative, the video recording of the earlier surgical procedure can be communicated by database 830 to teleoperated surgical system 850, and made available for viewing preoperatively or intraoperatively. In one aspect, the video recording is displayed by teleoperated surgical system 850 on a display located on surgeon's console 52. In another aspect, the video recording of the first surgical procedure is displayed on a display located on electronics cart 56.

Cloud-Based Video Database

In one aspect, database 830 is implemented on a remote server using a cloud data storage service and is accessible by multiple health care providers. Referring to FIG. 8, as shown by dashed line, surgical planning tool 800 optionally includes teleoperated surgical system 850 (as indicated by dashed line) and personal computer 840 (as indicated by dashed line). In one aspect, teleoperated surgical system 850 is similar to teleoperated surgical system 50 and personal computer 840 is similar to personal computer 820, except that teleoperated surgical system 50 and personal computer

820 are located at a first health care provider and teleoperated surgical system 850 and personal computer 840 are located at a second health care provider. In one aspect, a first patient requires surgical treatment of a medical condition, and undergoes a surgical procedure using teleoperated surgical system 50 at the first health care provider. A video recording of the surgical procedure is archived on database 830. At a later time, a second patient requires surgical treatment of the same medical condition, and plans to receive surgical treatment using teleoperated surgical system 850 at the second health care provider. Prior to performing the surgical procedure on the second patient, a medical person accesses database 830 through a secure internet connection and searches database 830 for surgical site video recordings of similar procedures. In one aspect, the medical person treating the second patient is able to retrieve from database 830 the video recording of first patient's surgical procedure, without acquiring knowledge of the identity of the first patient. In this manner, the privacy of the first patient is maintained. In one aspect, the video recording of the first patient's surgical procedure includes highlights and/or annotations made by the medical person who treated the first patient.

Computer Based Pattern Matching and Analysis

Surgical planning tool 800 can includes a pattern matching and analysis algorithm implemented in the form of computer executable code. In one aspect, the pattern matching and analysis algorithm is stored in a non-volatile memory device of surgical planning tool 800, and is configured to analyze the video recordings archived in database 830. As discussed previously, each of the video recordings archived in database 830 can be tagged and/or embedded with certain metadata information. This metadata information can include patient information such as patient age, gender, and other information describing the patient's health or medical history. Additionally, as discussed previously, the metadata information can include highlights or annotations made by a medical person. In one aspect, these highlights and annotations are embedded with the video recording and archived together with the video in database 830. The meta-data could also include either objective or subject grading of the skill of the surgical execution, such that such a pattern-matching algorithm could be designed to choose best matches representing a highest level of surgical skill.

In one aspect, pattern matching and analysis algorithm includes an image analysis component that identifies patterns in shapes and colors that are shared amongst multiple video recordings stored on database 830. The pattern matching and analysis algorithm then reviews the tagged metadata associated with this subset of video recordings to determine whether any words or phrases are frequently associated with videos within this subset. These analyses performed by pattern matching and analysis algorithm can be used to assist medical persons in making determinations about patient anatomy, preferred surgical approaches, co-morbidities, disease states, potential complications, etc.

A Method of Using a Surgical Planning Tool

Figure 9:
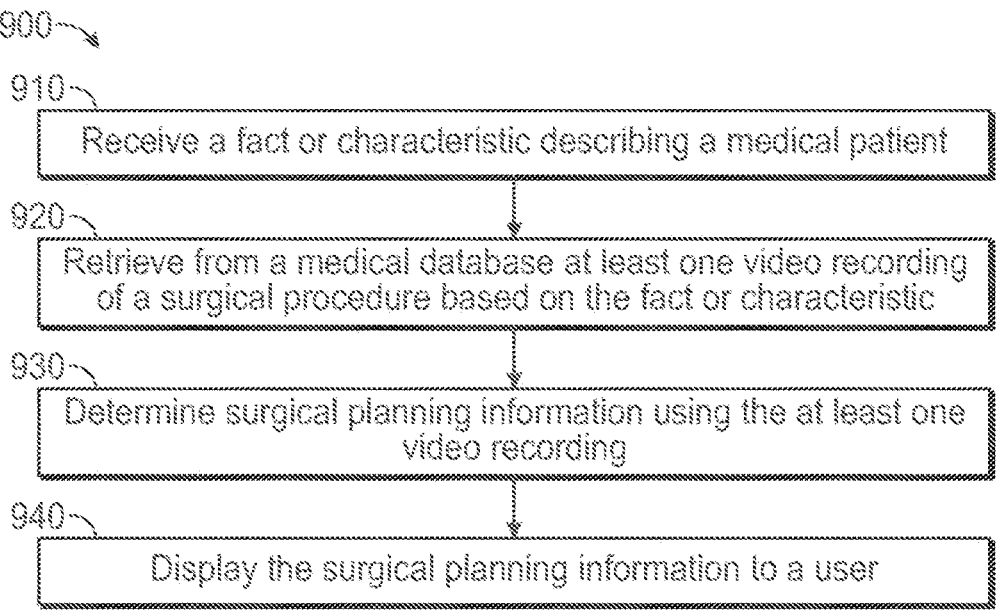
FIG. 9 is a flow diagram of a method of using a surgical planning tool.

FIG. 9 shows a method 900 of using a surgical planning tool. In one aspect, the surgical planning tool is similar to surgical planning tool 800 at FIG. 8. At 910, a fact or characteristic describing a medical patient, e.g., a medical condition suffered by a patient, is received by a medical device. Medical device can receive this fact or circumstance via a user interface located on a teleoperated surgical system (e.g., teleoperated surgical system 10 at FIG. 1 or teleoperated surgical system 50 at FIG. 4), or alternatively, through a personal computer similar to personal computer 820 at FIG. 2. At 920, the medical device uses the fact or characteristic received at 910 to retrieve at least one relevant video recording of a surgical procedure from a medical device database. At 930, the medical device uses the video recordings to determine surgical planning information. In one aspect, the surgical planning information includes the types of instruments used in the recorded procedure. At 940, the medical device displays to a user the surgical planning information determined at 930.

A Method of Using Patient Health Records to Guide a Surgical Procedure

Figure 10:
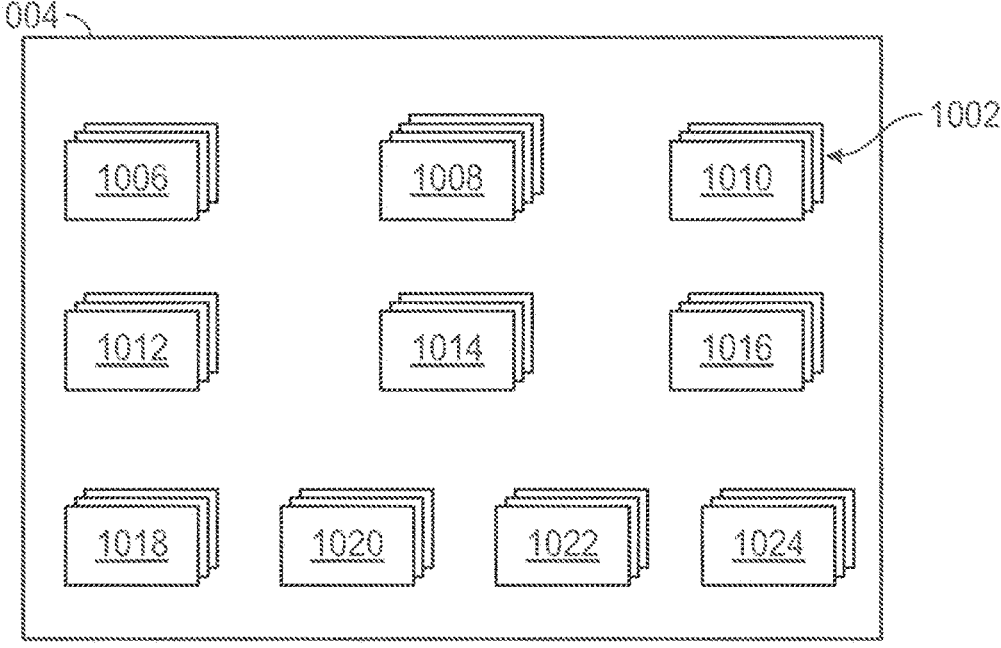
FIG. 10 is an illustrative drawing representing storage atlas information structure in a computer readable storage device in accordance with some embodiments.

FIG. 10 is an illustrative drawing representing storage atlas in a computer readable storage device 1004 in accordance with some embodiments. The storage atlas 1002 includes first information structures 1006 relating to prior surgical procedures, second information structures 1008 relating to teleoperated medical device operation, third information structures 1010 associating surgical procedures with the surgical instrument actuation during surgical procedures, fourth information structures 1012 relating patient health records to surgical procedures and fifth information structures 1014 relating patient health records to surgical instrument actuation during medical procedures. In some embodiments the storage atlas 1002 includes sixth information structures 1016 that provide a correlation between surgical patient risks and surgical patient health records. In some embodiments the storage atlas 1002 includes seventh information structures 1018 that provide a correlation between video images of surgical procedure stages and surgical instrument actuator states during surgical procedures.

In some embodiments, information in the various information structures 1004-1020 is evaluated to identify correlations between patient health records and surgical procedure results/risks. In some embodiments, information in the various information structures 1004-1020 is evaluated to identify correlations between patient safety concerns/risks and stages of a surgical procedure. In some embodiments, teleoperated surgical procedures are evaluated to identify correlations between patient safety concerns/risks and surgical instrument actuation state. These evaluations may involve machine learning (ML) techniques, for example. In some embodiments the storage atlas 1002 includes eighth information structures 1020 provide a correlation between surgical outcomes/risks and surgical instrument actuator states.

The storage atlas 1002 includes data concerning patients and surgeries. In some embodiments, the storage atlas 1002 includes video images of surgical scenes and corresponding annotations such as text and telestration tags 1022. In some embodiments, the storage atlas 1002 includes storage atlas 1002 includes recordings 1024 of surgical instrument actuator states during surgical procedures.

Figures 11, 12A, 12B, 12C:
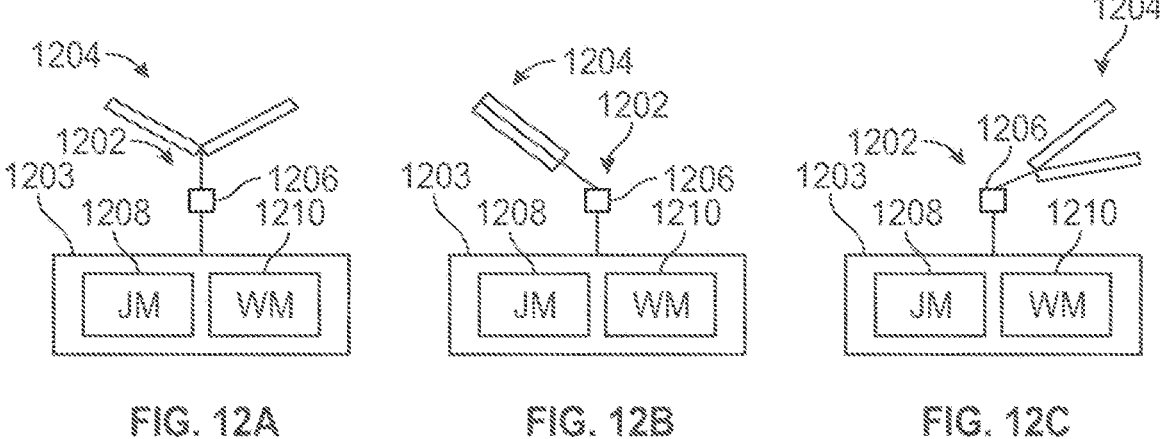
FIG. 11 is an illustrative drawing representing an example of the seventh information structure included within the atlas in the storage device, which associates recorded video information from an individual surgery with corresponding surgical instrument actuator state information in accordance with some embodiments.
FIGS. 12A-12C are illustrative drawings showing an example surgical instrument and an example actuator assembly in which the surgical instrument is shown in three different example operational states in accordance with some embodiments.

FIG. 11 is an illustrative drawing representing an example of the seventh information structure 1018 included within the atlas 1002 in the storage device 1004, which associates recorded video information from an individual surgery with corresponding surgical instrument actuator state information in accordance with some embodiments. In one aspect, video recording images during a surgery and surgical instrument actuator states are be time stamped (t1, t2 . . . tn) so as to produce a chronological record of times of occurrence of events shown within the video images and to provide a corresponding chronological record of times of occurrence of surgical instrument actuator states during a surgical procedure. Thus, time stamps recorded during a surgical procedure are used to temporally align video images with surgical instrument actuator states.

During a surgery, a user may annotate the video recording and the machine surgical instrument actuation state recording with metadata that indicate the stage of surgery. The annotation may include one or more of or a combination of written notes tagged to video information and/or surgical instrument actuation state information, coloring or highlighting (e.g., telestration) of images in the video recordings, for example. The annotations may be time stamped for use to temporally correlate them with corresponding video recording information and corresponding recorded machine tool state information.

Surgical procedures may be associated with surgical risks. Some surgical risks are more strongly associated with a certain stage of a medical procedure. In some embodiments, different stages of a surgery are demarcated by use of different surgical instruments during different stages. Moreover, some patients who have medical conditions that place them at a greater surgical risk than others during certain stages of a surgical procedure. For example, during a surgical procedure, a patient having chronic hypertension is at greater risk of stroke during a stage of the procedure requiring Trendelenburg position than a patient without the condition.

In a teleoperated surgical system, different instruments may be used at different stages of a surgical procedure. Moreover, the same instrument may be used in different actuator states at different stages of a surgical procedure. Thus, in some surgeries, a change in instrument signifies a transition to a different surgical stage, which correspond to a different level of risk, and in some surgical procedures a change in surgical instrument actuator state signifies a transition to a different surgical stage, which correspond to a different level of risk. As used herein, the term actuator state refers to a mechanical disposition of a surgical instrument as determined by an actuator, such as a motor, in response to input commands received from a surgeon or other surgical team member.

FIGS. 12A-12C are illustrative drawings showing an example surgical instrument 1202 and an actuator assembly 1203 in which the surgical instrument is shown in three different example operational states in accordance with some embodiments. The example instrument 1202 includes a jaw end effector 1204 that can transition between open and closed states and a continuum of partially opened/partially closed states in between. The example instrument 1202 also includes a two degree of freedom (2-dof) wrist 1206 that can move between different two-dimensional (x, y) positional states. The example actuator assembly 1203 includes a first actuator 1208, which in some embodiments includes a jaw motor (JM) used to actuate the jaw end effector 1204. The example actuator assembly 1203 includes a second actuator 1210, which in some embodiments includes a wrist motor (WM) used to actuate the wrist 1206. During a surgery, the surgical instrument 1202 may transition through multiple actuation states corresponding to different stages of a surgical procedure. As represented in FIG. 12A, for example, a surgical procedure may involve a first stage in which the first actuator 1208, the JM, disposes the jaw end effector 1204 to a fully open state and the second actuator 1210, the WM, disposes the wrist 1206 to a first positional state (x1, y1). As represented in FIG. 12B, for example, the surgical procedure may involve a second stage in which the first actuator 1208 transitions the jaw end effector 1204 to a fully closed state and the second actuator 1210 transitions the wrist 1206 to a second positional state (x2, y2). As represented in FIG. 12C, for example, the surgical procedure may involve a third stage in which the first actuator 1208 disposes the jaw end effector 1104 in a partially open/partially closed state and the second actuator 1210 transitions the wrist 1206 to a third positional state (x3, y3).

A surgeon may tailor a surgical procedure based upon a medical condition of a surgical patient as indicated by the patient's health records. A surgeon may take precautions during a surgical procedure to reduce the risk to a patient based upon the patient's health records. For example, a patient's health record may indicate suffers from a condition, which correlates to a surgical risk during a stage of a teloperated surgical procedure. Precautions that may be taken to reduce the risk to such a patient during a stage of a teleoperated surgical procedure include controlling actuation of an instrument, for example.

FIG. 13 is an illustrative drawing representing an example eighth information structure 1020 of the atlas 1002 stored in the computer readable storage device 1004 that corresponds to a particular surgical procedure and that associates different example surgical patient health record characteristics with surgical risk management information in accordance with some embodiments. A first column of the information structure 1020 indicates a list of patient health record (HR) characteristics; 1, 2, 3, 4, and 5. A second column of the information structure 1020 indicates surgical risks associated with an HR characteristic at a stage of the surgical procedure. Specifically, for example, HR characteristic 1 is associated with Risk 1 in stage 1 of the surgical procedure; HR characteristic 3 is associated with Risk 2 in stage 3 of the surgical procedure; and HR characteristic 5 is associated with Risk 3 in stage 5 of the surgical procedure. A third column of the information structure 1020 indicates surgical instrument actuation state during surgical stages when an HR characteristic is associated with an increased risk. For example, HR characteristic 1 is associated with surgical instrument actuator state X; HR characteristic 3 is associated with surgical instrument actuator state Y; and HR characteristic 5 is associated with surgical instrument actuator state Z. A fourth column of the information structure 1020 indicates messages to be presented to a surgical team at different stages of a surgical procedure, based upon HR characteristics. For example, HR characteristic 1 is associated with message A, which is associated with stage 1 and surgical actuation state X; HR characteristic 3 is associated with message B, which is associated with stage 3 and surgical actuation state Y; and HR characteristic 5 is associated with message B, which is associated with stage 5 and surgical actuation state Z. A fifth column of the information structure 1020 indicates surgical instrument actuator safety modes to be used at different stages of a surgical procedure, based upon HR characteristics. For example, HR characteristic 1 is associated with safety mode L, which is associated with stage 1 and surgical actuation state X; HR characteristic 3 is associated with safety mode M, which is associated with stage 3 and surgical actuation state Y; and HR characteristic 5 is associated with safety mode N, which is associated with stage 5 and surgical actuation state Z.

Referring to the first row of the example eighth information 1020 structure of FIG. 13, for example, during a colon resection surgical procedure stage 1 of the surgery may involve dissection. Risk 1 may involve injury to ureters or bladder due to adhesions from pervious surgeries, as indicated by the EHR. Message A may indicate mobilization of the bowel should be limited until complete exposure is established. Surgical instrument safety actuation state L may involve reducing the force available to the instrument arms to a level less than that which is available during normal non-safety mode operation, thereby limiting possible mobilization damage.

Referring to the third row of the example eighth information 1020 structure of FIG. 13, for example, during a prostatectomy surgical procedure stage 3 of the surgery may involve dissection near the nerves responsible for potency and continency. Risk 2 may involve nerve damage due to application of cautery energy nearby. Message B may indicate the presence of nerve tissue within a predefined range of a cautery instrument. Surgical instrument safety actuation state M may involve preventing actuation of the cautery energization function.

Referring to the fifth row of the example eighth information 1020 structure of FIG. 13, for example, during the surgical procedure involving liver tumor resection, stage 5 of the surgery may involve dissection of the tumor mass. Risk 3 may involve injury of a large vessel in the liver near the mass. Message C may indicate that the vessel is predicted to be near the dissection progress as determined by pre-operative imaging mapped onto the current surgical image. Surgical instrument safety actuation state N may involve limiting the motion of the surgical instruments to a range less than that which is available during normal non-safety mode operation, so that they physically do not contact the artery.

Figure 14:
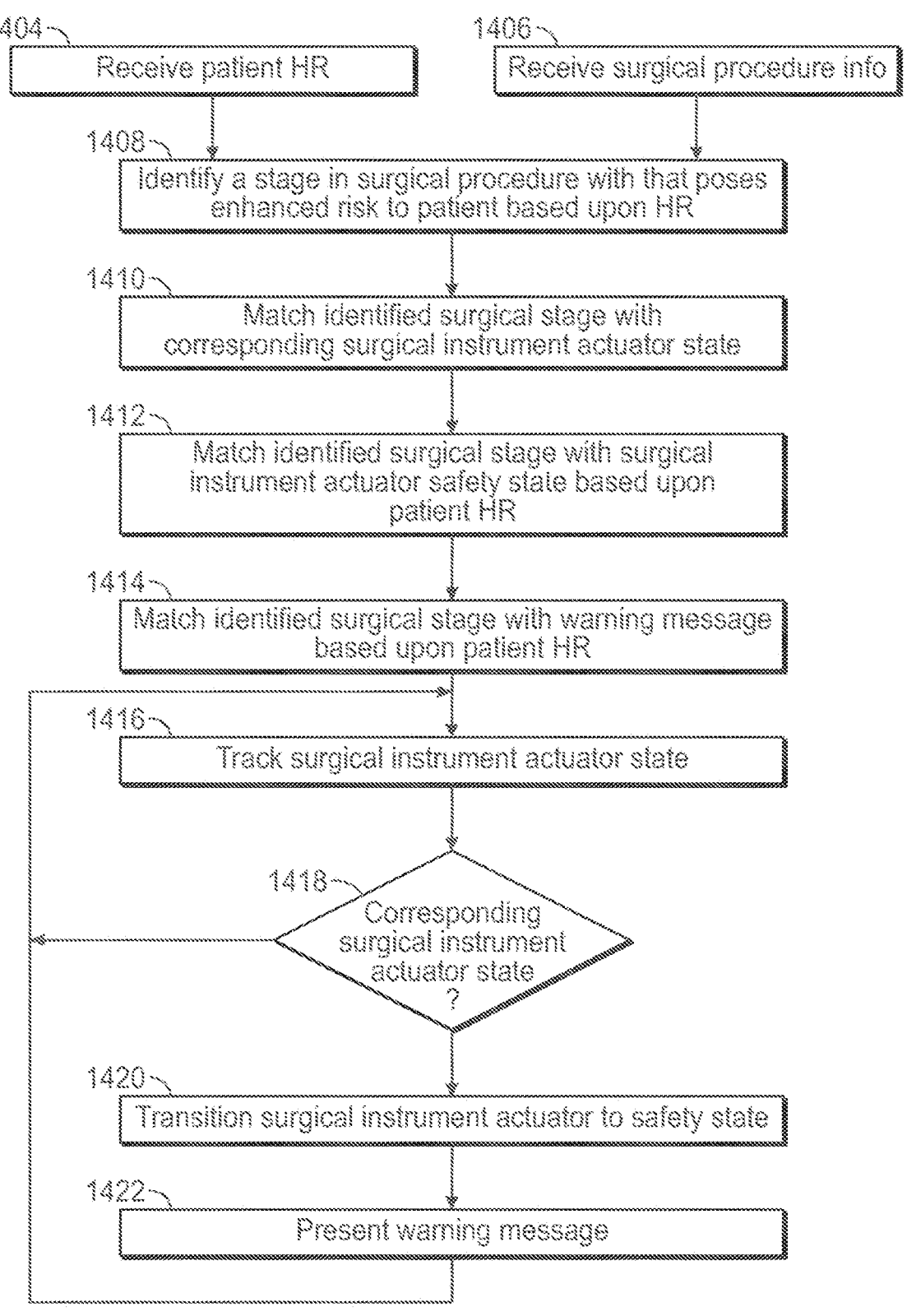
FIG. 14 is an illustrative flow diagram representing configuration of processor to present a warning message and to transition a surgical instrument to a safety state based at least in part upon a surgical patient's health record information in accordance with some embodiments.

FIG. 14 is an illustrative flow diagram representing configuration of processor 58 to perform a process 1402 to present a warning message and to transition a surgical instrument to a safety mode based at least in part upon a surgical patient's health record information in accordance with some embodiments. Computer program code is used in some embodiments to configure one or more CPUs of the processor 58 to perform the process 1402. In block 1404, a surgical patient's health record (HR) information is received at an input to a computer processing system associated with the electronics cart 56. In block 1406 surgical procedure information that indicates one or more surgical stages of a surgical procedure is received at an input of the computer processing system associated with the electronics cart 56. For some instruments used during a surgical procedure, a transition to use of the instrument indicates a transition to a different surgical stage. For some instruments used during a surgical procedure, a transition to a different actuator state of the instrument indicates a transition to a different surgical stage. In block 1408, the example eighth information structure 1020 of FIG. 13 is used to match HR characteristics of the received patient HR information with one or more surgical procedure stages in order to identify one or more surgical procedure stages in which the patient is at increased risk. In block 1410, the example eighth information structure 1020 is used to match the one or more identified surgical procedure stages in which a patient is at increased risk with surgical instrument actuator state information indicative of the one or more identified stages. In block 1412, the example eighth information structure 1020 is used to match the one or more identified surgical procedure stages in which a patient is at increased risk with one or more corresponding warning messages for presentation to a surgical team. In block 1414, the example eighth information structure 1020 is used to match the one or more identified surgical procedure stages in which a patient is at increased risk with information for corresponding surgical instrument safety actuation states.

During the performance of the surgical procedure, block 1416 tracks operational state of a surgical instrument actuator to determine, based upon the surgical instrument actuator state information determined in block 1410, when the surgical procedure is transitioning to a stage identified in block 1408 in which a patient having the received HR characteristics is at increased risk. In decision block 1418, a determination is made as to whether a current instrument actuator state matches the identified actuator state identified in block 1410. In response to no match, control loops back to block 1416 and tracking continues. In response to a match, block 1420 uses the identified actuator safety mode control information identified in block 1312 to transition the surgical instrument actuator to a safety mode operation to reduce the risk to a patient having the received health care record. Block 1422 configures the display device 32, 34 and/or 60 to present to a surgical team a message regarding the possible increased risk to a patient with the received health care record during the identified stage of the surgical procedure. In some embodiments, control next may flow back to block 1416, which may continue to track surgical instrument actuator state based upon other identified actuator state transition information, for example.

Although illustrative embodiments have been shown and described, a wide range of modification, change and substitution is contemplated in the foregoing disclosure and in some instances, some features of the embodiments may be employed without a corresponding use of other features. For example, in some embodiments, the processor 58 is coupled to a memory device such as storage device 1004 that includes instructions to implement a virtual surgical system that includes a virtual surgical instrument and a virtual surgical instrument actuator. The memory device 1004 includes an instruction set executable on the processor 58 to cause the processor 58 to perform operations. In some embodiments, the operations include receiving user input commands from a user to control movement of a first virtual robotic surgical instrument. The operations further include tracking virtual surgical instrument actuator state of the first virtual robotic instrument during movement of the first virtual robotic surgical instrument in response to the user input commands. The operations still further include transitioning the virtual surgical instrument actuator state of the first virtual robotic instrument to a first safety mode in response to the first virtual robotic surgical instrument transitioning to a first actuator state.

Moreover, in some embodiments the operations include receiving at an electronic user interface, health record information of a surgical patient that includes a first health feature. The operations further include matching within a computer readable storage device, the received first health feature with the first virtual actuator state of the virtual surgical instrument and matching within the storage device 1004, the received first health feature with a first message. The operations further include receiving user input commands from a user to control movement of a first virtual robotic surgical instrument. The operations further include tracking virtual surgical instrument actuator state of the first virtual robotic instrument during movement of the first virtual robotic surgical instrument in response to the user input commands. The operations further include transitioning the virtual surgical instrument actuator state of the first virtual robotic instrument to a first safety mode in response to the first virtual robotic surgical instrument transitioning to a first virtual actuator state. The operations further include displaying a first message on a user device display in response to the first virtual robotic surgical instrument transitioning to a first virtual actuator state.

One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A method of transitioning a surgical system to a safety mode operation, the method comprising:

identifying, by the one or more processors, a health record of a surgical patient that identifies one or more health characteristics of the surgical patient;

identifying, by the one or more processors based at least on a first health characteristic of the one or more health characteristics of the surgical patient, a first surgical stage of a plurality of stages of a surgical procedure to be performed using one or more robotic surgical instruments that poses an enhanced risk to the surgical patient;

identifying, by the one or more processors, that the first surgical stage of the surgical procedure is associated with the first actuation state of plurality of actuation states of a robotic surgical instrument of the one or more robotic surgical instrument and the first safety actuation state of the robotic surgical instrument;

identifying, by the one or more processors, that the first robotic surgical instrument transitioned to the first actuation state;

matching the first surgical stage with the first health characteristic of the surgical patient;

determining that the first actuation state of the first robotic instrument matches the first safety actuation state of the robotic surgical instrument associated with the first surgical stage; and causing, responsive to the determination, the robotic surgical instrument to transition to a safety mode operation identified by the first safety actuation state associated with the first actuation state.

2. The method of claim 1, further comprising receiving, by the one or more processors via a user interface, surgical procedure information that identifies the plurality of surgical stages of the surgical procedure.

3. The method of claim 1, further comprising receiving, by the one or more processors via a user interface, the health record of the surgical patient.

4. The method of claim 1, further comprising receiving, by the one or more processors, input commands from a user to control movement of the robotic surgical instrument.

5. The method of claim 1, further comprising tracking, by the one or more processors, surgical instrument actuation state of the robotic instrument during movement of the robotic surgical instrument in response to the input commands.

6. The method of claim 1, further comprising using, by the one or more processors, to match the first surgical stage with the first health characteristic of the surgical patient, one or more information structures that associate the plurality of actuation states with the plurality of safety actuation states for one or more of the plurality of surgical stages with one or more health characteristics of the surgical patient and one or more enhanced risks related to the one or more health characteristics of the surgical patient.

7. The method of claim 1, further comprising using, by the one or more processors, to match the first safety actuation state of the robotic surgical instrument associated with the first surgical stage, one or more information structures that associate the first health characteristic of the one or more health characteristics of the surgical patient with each of: the first surgical stage of the multiple stages of the surgical procedure, the enhanced risk of the one or more enhanced risks associated with the one or more health characteristics of the surgical patient, the first actuation state and the first safety actuation state.

8. A surgical system comprising:

one or more processors, coupled to memory, and configured to:

identify a health record of a surgical patient that identifies one or more health characteristics of the surgical patient;

identify, based at least on a first health characteristic of the one or more health characteristics of the surgical patient, a first surgical stage of a plurality of stages of a surgical procedure to be performed using one or more robotic surgical instruments that poses an enhanced risk to the surgical patient;

identify that the first surgical stage of the surgical procedure is associated with the first actuation state of plurality of actuation states of a robotic surgical instrument of the one or more robotic surgical instrument and the first safety actuation state of the robotic surgical instrument;

identify that the first robotic surgical instrument transitioned to the first actuation state;

match the first surgical stage with the first health characteristic of the surgical patient;

determine that the first actuation state of the first robotic instrument matches the first safety actuation state of the robotic surgical instrument associated with the first surgical stage; and cause, responsive to the determination, the robotic surgical instrument to transition to a safety mode operation identified by the first safety actuation state associated with the first actuation state.

9. The surgical system of claim 8, wherein the one or more processors are further configured to provide user interface via which to receive surgical procedure information that identifies the plurality of surgical stages of the surgical procedure.

10. The surgical system of claim 8, wherein the one or more processors are further configured to provide a user interface via which to receive the health record of the surgical patient.

11. The surgical system of claim 8, wherein the one or more processors are further configured to receive input commands from a user to control movement of the robotic surgical instrument.

12. The surgical system of claim 8, wherein the one or more processors are further configured to track surgical instrument actuation state of the robotic instrument during movement of the robotic surgical instrument in response to the input commands.

13. The surgical system of claim 8, wherein the one or more processors are further configured to use one or more information structures to match the first surgical stage with the first health characteristic of the surgical patient, the one or more information structures that associate the plurality of actuation states with the plurality of safety actuation states for one or more of the plurality of surgical stages with one or more health characteristics of the surgical patient and one or more enhanced risks related to the one or more health characteristics of the surgical patient.

14. The surgical system of claim 8, wherein the one or more processors are further configured to use one or more information structures to match the first safety actuation state of the robotic surgical instrument associated with the first surgical stage, the one or more information structures that associate the first health characteristic of the one or more health characteristics of the surgical patient with each of: the first surgical stage of the multiple stages of the surgical procedure, the enhanced risk of the one or more enhanced risks associated with the one or more health characteristics of the surgical patient, the first actuation state and the first safety actuation state.

15. A non-transitory computer-readable medium comprising instructions configured to cause a surgical system to perform operations comprising:

identify a health record of a surgical patient that identifies one or more health characteristics of the surgical patient;

identify, based at least on a first health characteristic of the one or more health characteristics of the surgical patient, a first surgical stage of a plurality of stages of a surgical procedure to be performed using one or more robotic surgical instruments that poses an enhanced risk to the surgical patient;

identify that the first surgical stage of the surgical procedure is associated with the first actuation state of plurality of actuation states of a robotic surgical instrument of the one or more robotic surgical instrument and the first safety actuation state of the robotic surgical instrument;

identify that the first robotic surgical instrument transitioned to the first actuation state;

match the first surgical stage with the first health characteristic of the surgical patient;

determine that the first actuation state of the first robotic instrument matches the first safety actuation state of the robotic surgical instrument associated with the first surgical stage;

cause, responsive to the determination, the robotic surgical instrument to transition to a safety mode operation identified by the first safety actuation state associated with the first actuation state.

16. The non-transitory computer-readable medium of claim 15, further comprising instructions configured to cause the surgical system to provide a user interface via which to receive surgical procedure information that identifies the plurality of surgical stages of the surgical procedure or the health record of the surgical patient.

17. The non-transitory computer-readable medium of claim 15, further comprising instructions configured to cause the surgical system to track surgical instrument actuation state of the robotic instrument during movement of the robotic surgical instrument in response to the input commands.

18. The non-transitory computer-readable medium of claim 15, further comprising instructions configured to cause the surgical system to provide a user interface via which to receive the health record of the surgical patient.

19. The non-transitory computer-readable medium of claim 15, further comprising instructions configured to cause the surgical system to use one or more information structures to match the first surgical stage with the first health characteristic of the surgical patient, the one or more information structures that associate the plurality of actuation states with the plurality of safety actuation states for one or more of the plurality of surgical stages with one or more health characteristics of the surgical patient and one or more enhanced risks related to the one or more health characteristics of the surgical patient.

20. The non-transitory computer-readable medium of claim 15, further comprising instructions configured to cause the surgical system to use one or more information structures to match the first safety actuation state of the robotic surgical instrument associated with the first surgical stage, the one or more information structures that associate the first health characteristic of the one or more health characteristics of the surgical patient with each of: the first surgical stage of the multiple stages of the surgical procedure, the enhanced risk of the one or more enhanced risks associated with the one or more health characteristics of the surgical patient, the first actuation state and the first safety actuation state.

* * * * *